US00RE34712E

United States Patent [19]

Boegesoe et al.

[11] E Patent Number: Re. 34,712

[45] Reissued Date of Patent: Aug. 30, 1994

[54] PHARMACEUTICALLY USEFUL (+)-1-(3-DIMETHYLAMINOPROPYL)-1-(4'-FLUOROPHENYL)-1,3-DIHYDROISO BENZOFURAN-5-CARBONITRILE AND NON-TOXIC ACID ADDITION SALTS THEREOF

[75] Inventors: Klaus P. Boegesoe, Hørsholm; Jens K. Perregaard, J gerspris, both of Denmark

[73] Assignee: H. Lundbeck A/S, Copenhagen-Valby, Denmark

[21] Appl. No.: 122,009

[22] Filed: Sep. 14, 1993

Related U.S. Patent Documents

Reissue of:

[64] Patent No.: 4,943,590
Issued: Jul. 24, 1990
Appl. No.: 363,589
Filed: Jun. 8, 1989

[30] Foreign Application Priority Data

Jun. 14, 1988 [GB] United Kingdom ..... 8814057

[51] Int. Cl.[5] ..... A61K 31/34; C07D 307/87; C07C 255/59

[52] U.S. Cl. ..... 514/469; 549/467; 558/422

[58] Field of Search ..... 549/467; 558/422; 514/469

[56] References Cited

U.S. PATENT DOCUMENTS 4,136,193 1/1979 Boegesoe et al. ..... 549/467
4,650,884 3/1987 Boegesoe ..... 549/467

*Primary Examiner*—Bernard Dentz
*Attorney, Agent, or Firm*—Gordon W. Hueschen

[57] ABSTRACT

The two enantiomers of the anti-depressant drug of the formula I

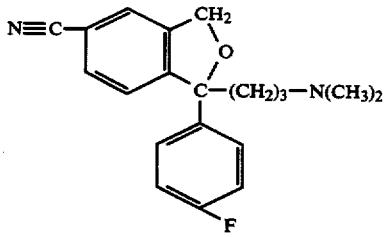

are disclosed. Methods for resolving intermediates and their [steroselective] *stereoselective* conversion to a corresponding [enatiomer] *enantiomer* of I are also disclosed.

12 Claims, No Drawings

PHARMACEUTICALLY USEFUL (+)-1-(3-DIMETHYLAMINOPROPYL)-1-(4'-FLUOROPHENYL)-1,3-DIHYDROISO BENZOFURAN-5-CARBONITRILE AND NON-TOXIC ACID ADDITION SALTS THEREOF

Matter enclosed in heavy brackets [ ] appears in the original patent but forms no part of this reissue specification; matter printed in italics indicates the additions made by reissue.

The present invention relates to the two novel enantiomers of the antidepressant drug 1-(3-dimethylaminopropyl)-1-(4'-fluorophenyl)-1,3-[dihydroisobenzofuran] *dihydroisobenzofuran*-b 5-carbonitrile (citalopram) of the following formula I:

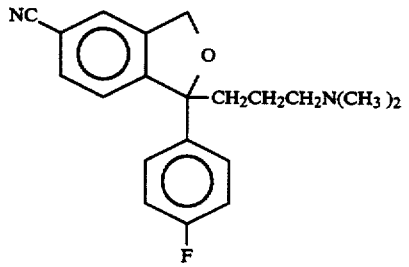

I and to the use of these enantiomers as antidepressant compounds as well as the possible use as geriatrics or in the cure of obesity or alcoholism.

This invention also includes pharmaceutically acceptable salts of the enantiomers of compound I formed with non-toxic organic or inorganic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqeuous immiscible solvent, such as ethyl ether, ethyl acetate or [dicloromethane] *dichloromethane*, with the desired salt separating directly. Exemplary of such organic ]salt] *salts* are those with maleic, fumaric, benzoic, ascorbic, pamoic, succinic, oxalic, salicylic, methanesulfonic, ethanedisulfonic, acetic, propionic, tartaric, citric, gluconic, lactic, malic, mandelic, cinnamic, citraconic, aspartic, stearic, palmitic, itaconic, glycolic, p-amino-benzoic, glutamic, benzene sulfonic and theophylline acetic acid, as well as the 8-halotheophyllines, for example 8-bromotheophylline.

Exemplary of such inorganic salts are those with hydrochloric, hydrobromic, sulfuric, sulfamic, phosphoric and nitric acids. Of course, these salts may also be prepared by the conventional method of double decomposition of appropriate salts, which is well-known to the art.

Furthermore it was found that non-hygroscopic acid addition salts might be obtained by [conventinal] *conventional* freeze drying techniques from water solutions of appropriate salts of the above mentioned kinds.

The invention is also concerned with a method to resolve the intermediate racemate and to produce the individual isomers of I therefrom.

BACKGROUND OF THE INVENTION

Citalopram, which has been disclosed in e.g. U.S. Pat. No. 4,136,193, has proven to be an efficient antidepressant compound in man (Ref.: A. Gravem et. al., Acta pysychiat. Scan., No. 75, p. 478–486 (1987). All work in the development of this compound has been made with the racemate. Citalopram has been shown pharmacologically to be a very selective inhibitor of 5-HT reuptake. Previous attempts to crystallize diastereomeric salts of citalopram enantiomers have failed.

SUMMARY OF THE INVENTION

Surprisingly, it has now proven possible to resolve the intermediate [4-(4-dimethylamino)-1-(4'-fluorophenyl)-1-(hydroxybutyl)-3-(hydroxymethyl)benzonitrile] *4-[4-(dimethylamino)-1-(4'-fluorophenyl)-1-hydroxy-1-butyl]-3-(hydroxymethyl)-benzonitrile*, II, into its enantiomers and finally in a stereoselective way to convert these enantiomers to the corresponding citalopram enantiomers. Likewise, monoesters of II formed by optically active carboxylic acids could be separated into the corresponding diastereomers and subsequently converted directly into citalopram enantiomers in a steroselective ringclosure reaction. The intermediate diol, II, has been disclosed in e.g. U.S. Pat. No. 4,650,884 as a racemic mixture.

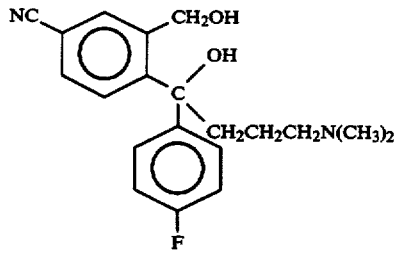

II

The enantiomers of the intermediate of formula II as well as monoesters fall likewise within the scope of the present invention.

Furthermore, it was shown to our surprise that almost the entire 5-HT uptake inhibition resided in the (+)-citalopram enantiomer.

The present invention also includes a new method of synthesizing I from the diol compound II by esterification of the primary alcohol group into a labile ester, which in the presence of a base undergoes spontaneous ringclosure to citalopram or, if enantiomerically pure II is esterified, the corresponding citalopram enantiomer is produced with fully conservation of stereoconfiguration.

According to the invention, II is reacted with:

(a) an enantiomerically pure acid derivative as an acid chloride, anhydride or [libile] *labile* ester as e.g. [examplified] *exemplified* in reaction scheme I by (+)- or (−) -α-methoxy-α-trifluoromethylphenylacetyl chloride. The reaction is preferably performed in an inert organic solvent as e.g. toluene, dichloromethane or tetrahydrofuran. A base (triethylamine, N,N-dimethylaniline, pyridin or the like) is added to neutralize liberated HCl. The diastereoisomers are subsquently separated by HPLC or fractional crystallization. The thus purified [disatereoisomers] *diastereoisomers*are [finnaly] *finally* separately treated with strong base (e.g. alkoxide) in an inert organic solvent as e.g. toluene, tetrahydrofuran, or dimethoxyethane yielding the pure citalopram enantiomers respectively. The ringclosure reaction is preferably performed at relatively low temperatures (−20° C.) to room temperature).

REACTION SCHEME I

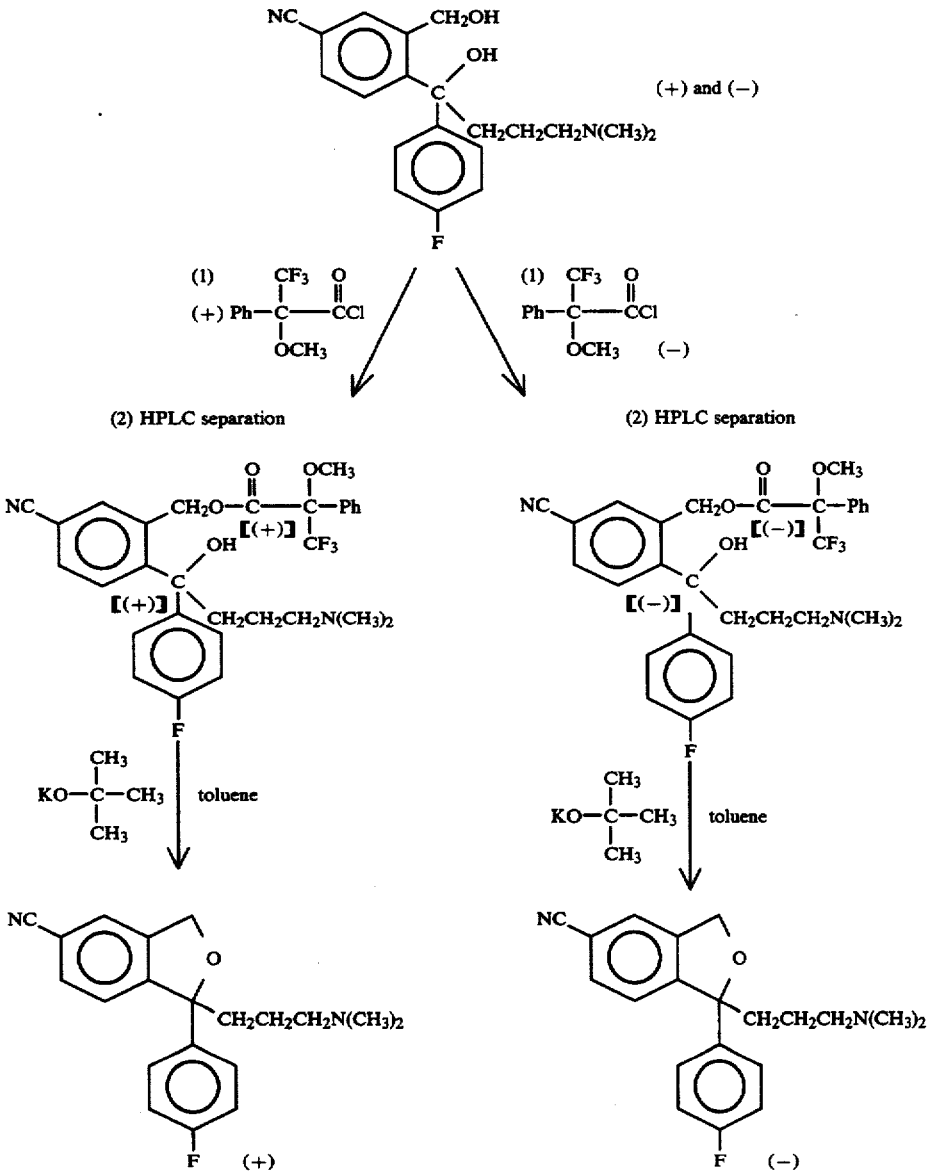

(b) the enantiomers of an optically active acid successively affording the pure diastereomeric salts. Optically antipodes of tartaric acid, di-benzoyltartaric acid, di-(p-[toloyl] *toluoyl*)tartaric acid, bisnaphthylphosphoric acid, 10-camphorsulphonic acid and the like are conveniently used.

(c) Stereoselective ringclosure of the pure enantiomers of II prepared as in (b) is performed via a labile ester as e.g. methansulfonyl, p-toluenesulfonyl, 10-camphorsulfonyl, trifuoracetyl or trifluoromethansulfonyl with simultaneous addition of a base (triethylamine, dimethylaniline or pyridin) in an inert organic solvent at 0° C. The ringclosure reaction is [examplified] *exemplified* in reaction scheme II:

REACTION SCHEME II

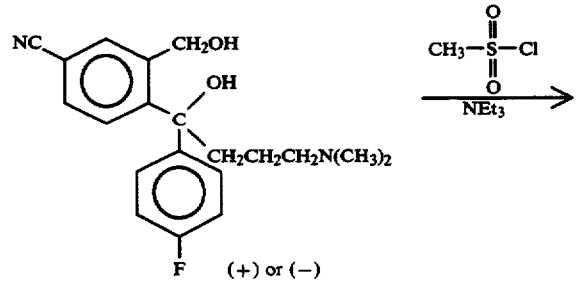

-continued

REACTION SCHEME II

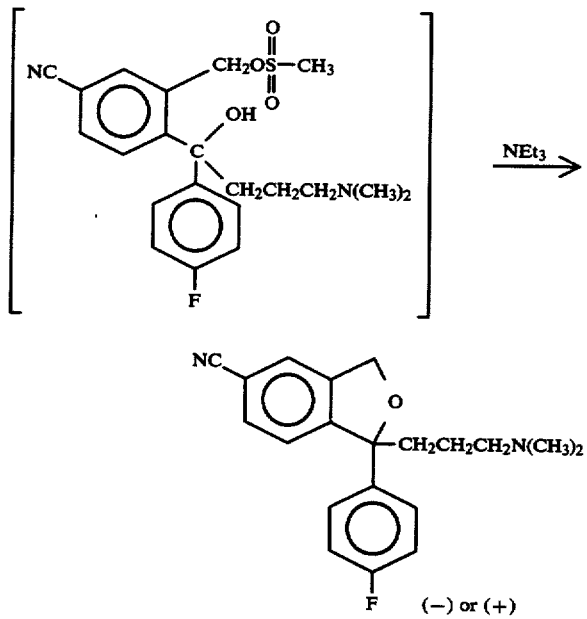

EXAMPLE 1

Resolution by method (a)

To 11 g of (+)-α-methoxy-α-trifluoromethylacetic acid dissolved in 25 ml of chloroform were added 50 ml of thionylchloride and a few drops of dimethylformamide. The reaction mixture was refluxed for 2 hours. Excess of thionylchloride was evaporated with toluene leaving the (+)-α-methoxy-α-trifluoromethylacetyl chloride as a liquid. This liquid diluted with 50 ml of dichloromethane was added dropwise to an ice cooled solution of 17 gr of [4-(4-dimethylamino-1-(4'-fluorophenyl)-1-hydroxybutyl)-3-(hydroxymethyl)-benzonitrile] *4-[4-(dimethylamino)-1-(4'-fluorophenyl)-1-hydroxy-1-butyl]-3-(hydroxymethyl)-benzonitrile*, II, and 8 ml of triethylamine in 150 ml of dichloromethane. The reaction mixture was further stirred for another hour at room temperature, subsequently washed with brine, dried ($MgSO_4$) and the solvent evaporated below 30° C. in vacuo affording 29 gr of the ester as a diastereomeric mixture. By repeated HPLC purification (eluted with ethyl acetate/tetrahydrofuran 9:1 containing 4% of triethylamine) and by collecting only the 5–10% initial substance in the main peak, 1.1 gr of enantiomerically pure compound was isolated.

The substance thus isolated was dissolved in dry toluene (50 ml) and added to a suspension of 0.3 gr of potassium t-butoxide in 20 ml of toluene at 0° C. The toluene solution was washed with water, dried ($MgSO_4$) and the solvent evaporated yielding 0.6 gr of (+)-1-(dimethylaminopropyl)-1-(4'-fluorophenyl)-1,3-dihydroisobenzofuran-5-carbonitrile as an oil. $[\alpha]_D=+11.81°$ (c=1, $CH_3OH$) (determined with a substance containing 10% w/w of methanol). The optical purity was determined by $^1H$ NMR spectroscopy ($CDCL_3$ as solvent) (Bruker AC-250 MHz instrument) by addition of a 10:1 w/w surplus of the chiral reagent (−)-2,2,2-trifluoro-1-(9-anthryl)ethanol. Optical purity: 99.6%.

In a totally analogous way the (−)-1-(3-dimethylaminopropyl)-1-(4'-fluorophenyl)-1,3-dihydroisobenzofuran-5-carbonitrile was synthesized. $[\alpha]_D=-12.34°$ (c=1, $CH_3OH$) (determined with a substance containing 10% w/w of methanol). Optical purity: 99.0%.

EXAMPLE 2

Resolution by methods (b) and (c)

To a solution of 85 gr of [4-(4-dimethylamino)-1-4'-fluorophenyl)-1-(hydroxybutyl)-3-(hydroxymethyl)-benzonitrile] *4-[4-(dimethylamino)-1-(4'-fluorophenyl)-1-hydroxy-1-butyl]-3-(hydroxymethyl)-benzonitrile*, hydrobromide in 500 ml of water were added 200 ml of ice cooled 2M NaOH solution and 500 ml of ether. The mixture was stirred for ½ hour, the ether phase separated, dried ($MgSO_4$) and the ether evaporated. The remaining oil was dissolved in 400 ml of 2-propanol at 40° C., and 40 gr of (+)-di-p-[toloyltartaric] *toluoyltartaric* acid (as hydrate) were added under vigorous stirring. After a short while crystallization began. After 3 hours of stirring the precipatated salt was filtered off and dried yielding 29.2 gr (55.1%) of [(−)-4-(4-dimethylamino)-1-(4'fluorophenyl)-1-(hydroxybutyl)-3-(hydroxymethyl)benzonitrile] *(−)-4-[4-(dimethylamino)-1-(4'-fluorophenyl)-1-hydroxy-1-butyl]-3-(hydroxymethyl)benzonitrile*, hemi (+)-di-p-[toloyltartaric] *toluoyltartaric* acid salt. MP: 134°–135° C., $[\alpha]_D=+10.0°$ (c=1, $CH_3OH$). The filtrate is used below.

To an ice cooled solution of 14 gr of the (−)-isomer from above as a base in 300 ml of dry toluene were added 16 ml of triethylamine, and 3.6 ml of methansulfonyl chloride in 20 ml of dry toluene were added dropwise during 10 minutes. The reaction mixture was further stirred for ½ hour, washed with brine, dried ($MgSO_4$) and the solvent evaporated. The title compound was purified by column chromatography affording 8 g of (+)-1-(3-dimethylaminopropyl)-1-(4'-[flurophenyl] *fluorophenyl*-1,3-dihydroisobenzofuran-5-carbonitrile. $[\alpha]_D=+12.33°$ (c=1, $CH_3OH$). The oxalic acid salt of the (+)-isomer crystallized from acetone. MP: 147°–148° C., $[\alpha]_D=+12.31°$ (c=1, $CH_3OH$).

The pamoic acid salt of the (+)-isomer was prepared in the following manner: To 1.8 g of the base of the (+)-isomer was added 2 g of pamoic acid in 25 ml of MeOH. The mixture was refluxed for an hour and subsequently colled to room temperature. The precipitate was filtered off yielding 3.0 g of the pamoic acid salt. MP: 264°–266° C., $[\alpha]_D=+13.88°$ C. (c=1, dimethylformamide).

A 2:1 addition compound of the (+)-isomer with L(+)-tartaric acid was prepared in the following manner: 4 g of the (+)-isomer as base were dissolved in 100 ml of diethyl ether and extracted into 100 ml of water containing 0.8 g of L(+)-tartaric acid by stirring. The organic phase was separated and discarded. The water-phase was freeze-dried in vacuo (<0.1 mm Hg) for 18 hours leaving 3.8 g of a white powder of the title compound. This addition compound was stable and not hygroscopic.

In a corresponding manner as above via the [(+)-4-(4-dimethylamino)-1-(4'-fluorophenyl)-1-(hydroxybutyl)-3-(hydroxymethyl)benezonitrile] *(+)-4-[4-(dimethylamino)-1-(4'-fluorophenyl)-1-hydroxy-1-butyl]-3-(hydroxymethyl)-benzonitrile*, hemi (−)-di-(p-toloyl)-tartaric acid salt ($[\alpha]_D=-8.9°$ (c=1, $CH_3OH$)) which was converted to the corresponding diol base ($[\alpha]_D=+61.1°$ (c=1, $CH_3OH$)) and finally ringclosure reaction yielded 10 gr of (−)-1-(3-dimethylaminopropyl)-1-(4'-fluorophenyl)-1,3-dihydroisobenzofuran-5-carbonitrile. $[\alpha]_D = -12.1°$ (c=1, $CH_3OH$).

The oxalic acid salt of the (−)-isomer crystallized from acetone, MP: 147°-148° C., $[\alpha]_D = -12.08°$ (c=1, $CH_3OH$).

EXAMPLE 3

Preparation of citalopram by method (c)

To an ice cooled solution of 28 gr of racemic diol base, II, in 500 ml of dichloromethane were added 32 ml of triethylamine, and 7.5 ml of methansulfonyl chloride in 30 ml of dichloromethane were added dropwise during a half hour. The reaction mixture was washed with 0.1M NaOH solution twice, the organic phase separated, dried ($MgSO_4$) and the solvent evaporated, leaving 21.5 gr of the title (±)-citalopram as a crystalline base. The thus obtained material was dissolved in a mixture of 2-propanol and methanol (2:1) and an equivalent amount of gaseous HBr was introduced. The mixture was left overnight and the precipitated hydrobromide was filtered off. Yield: 26 gr with MP 184°-186° C.

The enantiomers from Example 1 were tested for their ability to block 5-HT reuptake in standard and reliable test method. Results are shown in Table I in comparison with the racemic mixture of citalopram.

5-HTP-POTENTIATION

The test evaluates the ability of the substance to potentiate the effect of 5-HTP, which results in development of 5-HT syndrome (Christensen, Fjalland, Pedersen, Danneskiold-Samsoe and Svendsen; European J. Pharmacol. 41, 153-162, 1977).

Procedure

Each treatment group consists of 3 mice, and two groups are treated with the highest test dose. A control group only treated with 5-HTP is included and a group treated with citalopram 10 mg/kg and 5-HTP is used as reference for full 5-HT syndrome.

The Route of Administration 30 minutes after the administration of the test substance, the other groups are given 5-HTP (100 mg/kg) i.v. (injection time 5-10 sec.). After this 5-HTP dose normal, untreated mice remain unaffected, but if the animals have been pretreated with a substance, which inhibits the uptake of 5-HT or a 5-HT agonist, a 5-HTP syndrome will occur. The symptoms are the same as previously described: (1) excitation, (2) tremor, and (3) abduction of the hind limbs. The animals are observed for 15 minutes and each animal is given one point for each symptom present. Again the result is stated in fractions: 0/9, 1/9, . . . 9/9, where 0, 1, . . . , 9 are the number of points per group after the dose in question. The $ED_{50}$ value is calculated by log-probit analysis.

INHIBITION OF $^3$H-SEROTONIN UPTAKE IN RAT BRAIN SYNAPTOSOMES

By this method the inhibition by drugs of the uptake of [$_3$H-serotonin] *$^3$H-serotonin* ($^3$H-5-HT)(10 nm) in rat brain synaptosomes is determined in vitro. Method and results in Hyttel, Psychopharmacology 1978, 60, 13-18; Hyttel, Prog. Neuro-Psychopharmacol. & Biol. [Psychait.] *Psychiat.* 1982, 6,277-295; Hyttel & Larsen, Acta pharmacol. tox. 1985, 56, suppl. 1, 146-153. [Procedure p]

*Procedure*

Male Wistar (Mol: Wist) rats (125-250 g) are sacrified by decapitation and [exanguinated] *exsanguinated* Brain tissue (minus cerebellum) is gently homogenized (glass teflon homogenizer) in 40 vol (w/v) of ice cold 0.32M of sucrose containing 1 mM of nialamide. The $P_2$ fraction (synaptosomal fraction) is obtained by centrifugation (600 g. 10 min and 25000 g. 55 min, 4° C.) and suspended in 800 volumes of a modified Krebs-Ringer-phosphate buffer, pH 7.4.

To 4000 μl of the synaptosomal suspension (5 mg original tissue) on ice are added 100 μl test substance in water. After preincubation at 37° C. for 5 min, 100 μl of $^3$H-1-NA (final [concnetration] *concentration* 10 nM) are added and the samples are incubated for 10 min at 37° C. The incubation is terminated by filtering the samples under vacuum through [Whatmam] *Whatman* GF/F filters with a wash of 5 ml buffer containing 10 μM of unlabeled 5-HT. The filters are placed in counting vitals and 4 ml of appropriate scintillation fluid (e.g. Picofluor ®15) are added. After shaking for 1 h and storage 2 h in the dark the content of radioactivity is determined by liquid scintillation counting. Uptake is obtained by subtracting the nonspecific binding and passive transport measured in the presence of 10 μM citalopram (Lu 10-171-B).

For determination of the inhibition of uptake five concentrations of drugs covering 3 decades are used.

The measured cpm are plotted against drug concentration on semilogarithmic paper, and the best fitting s-shaped curve is drawn. The $IC_{50}$-value is determined as the concentration, at which the uptake is 50% of the total uptake in control samples minus the nonspecific binding and uptake in the presence of 10 μM of citalopram.

TABLE 1

PHARMACOLOGICAL TEST RESULTS

| Compound | 5-HTP pot. $ED_{50}$ μmol/kg | 5-HT uptake inhibition $IC_{50}$ (nM) |
|---|---|---|
| (+)-citalopram | 2.0 | 1.1 |
| (−)-citalopram | 120 | 150 |
| (±)-citalopram | 3.3 | 1.8 |

(+)-1-(3-Dimethylaminopropyl)-1-(4'-fluorophenyl)-1,3-dihydroisobenzofuran-5-carbonitrile ((+)-citalopram) and the non-toxic acid addition salts thereof may be administered to animals such as dogs, cats, horses, sheeps or the like, including human beings, both orally and parenterally, and may be used for example in the form of tablets, [capsles] *capsules*, powders, syrups or in the form of the usual [sterial] *sterile* solutions for injection. [Results upon administration to human being have been very gratifying.]

Most conveniently the compounds of Formula I are administered orally in unit dosage form such as tablets or capsules, each dosage unit containing the free amine or a non-toxic acid addition salt of one of the said compounds in [a] *an* amount of from about 0.10 to about 100 mg, most preferably, however, from about b 5 to 50 mg, calculated as the free amine, the total daily dosage usually ranging from about 1.0 to about 500 mg. The exact individual dosages as well as daily dosages in a particular case will, of course, be determined according to established medical principles under the direction of a physician.

When preparing tablets, the [acitve] *active* ingredient is for the most part mixed with ordinary tablet adjuvants such as corn starch, potato starch, talcum, magnesium stearate, gelative, lactose, gums, or the like.

Typical examples of formulas for [composition] *compositions* containing (+)-citalopram in the form of an acid addition salt as the active ingredient, are as follows:

| | |
|---|---|
| (1) Tablets containing 5 milligrams of (+)-citalopram calculated as the free base: | |
| Compound 20 | 5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |
| (2) Tablets containing 50 milligrams of (+)-citalopram calculated as the free base: | |
| (+)-citalopram | 50 mg |
| Lactose | 16 mg |
| Potato starch | 45 mg |
| Saccharose | 106 mg |
| Sorbitol | 6 mg |
| Talcum | 9 mg |
| Gelatine | 4 mg |
| Povidone | 3 mg |
| Magnesium stearate | 0.6 mg |
| (3) Syrup containing per milliliter: | |
| (+)-citalopram | 10 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water ad | 1 ml |
| (4) Solution for injection containing per milliliter: | |
| (+)-citalopram | 50 mg |
| Acetic acid | 17.9 mg |
| Sterile water ad | 1 ml |
| (5) Solution for injection containing per milliliter: | |
| (+)-citalopram | 10 mg |
| Sorbitol | 42.9 mg |
| Acetic acid | 0.63 mg |
| Sodium hydroxide | 22 mg |
| Sterile water ad | 1 ml |

Any other pharmaceutical tableting adjuvants may be used provided that they are compatible with the active ingredient, and additional compositions and dosage forms may be similar to those presently used for neuroleptics, analgesics or antidepressants.

Also combinations of (+)-citalopram as well as its non-toxic acid salts with other active ingredients, especially other neuroleptics, thymoleptics, tranquilizers, analgetics or the like, fall within the scope of the present invention.

As previously stated, when isolating the enantiomers of citalopram in the form of an acid addition salt the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethane-sulphonates, lactates, citrates, tartrates or bitartrates, pamoates and maleates of the amines of Formula I. Other acids are likewise suitable and may be employed if desired. For example: fumaric, benzoic, ascorbic, succinic, salicylic, bismethylenesalicylic, propionic, gluconic, malic, malonic, mandelic, [cannamic] *cinnamic*, citraconic, stearic, palmitic, itaconic, glycolic, benzenesulphonic, and sulphamic acids may [be ] also be employed as acid addition salt-forming acids.

When it is desired to isolate a compound of the invention in the form of the free base, this may be done according to conventional procedure as by dissolving the isolated or unisolated salt in water, treating with a suitable alkaline material, extracting the liberated free base with a suitable organic [solvent] *solvent*, drying the extract and evaporating to dryness or fractionally distilling to effect isolation of the free basic amine.

The invention also comprises a method for the alleviation, palliation, mitigation or inhibition of the manifestations of certain physiological-psychological [abnormalies] *abnormalities* of animals, especially depressions, by administering to a living animal body, including human beings, an adequate quantity of (+)-citalopram or a non-toxic acid addition salt thereof. An adequate quantity would be from about 0.001 mg to about 10 mg per kg of body weight in each unit dosage, and from about 0.003 milligrams to about 7 milligrams/kg of body weight per day.

It is to be understood that the invention is not limited to the exact details of operation or exact [compound] *compounds* or compositions shown and described, as obvious modifications and equivalents will be apparent to one skilled in the art.

We claim:

1. A compound selected from substantially pure (+)-1-(3-Dimethylaminopropyl)-1-(4'- fluorophenyl)-1,3-dihydroisobenzofuran-5-carbonitrile and non-toxic acid addition salts thereof.

2. A compound of claim 1 being *the* pamoic acid salt of substantially pure (+)-1-(3-dimethylaminopropyl)-1-(4'-fluorophenyl)-1,3-dihydroisobenzofuran-5-carbonitrile.

3. A pharmaceutical composition in unit dosage form comprising a pharmaceutically acceptable diluent or adjuvant and, as an active ingredient, a compound as defined in claim 1.

4. A pharmaceutical composition in unit dosage form comprising a pharmaceutically acceptable diluent or adjuvant and, as an active ingredient, the compound of claim 2.

5. A pharmaceutical composition in unit dosage form, according to claim 3, wherein the active ingredient is present in an amount from 0.1 to 100 milligram per unit dose.

6. A pharmaceutical composition in unit dosage form, according to claim 4, wherein the active ingredient is present in an amount from 0.1 to 100 milligram per unit dose.

7. A method for the alleviation of depression in a living animal body subject thereto which comprises the step of administering to the living animal body an amount of a compound of claim 1 which is effective for said purpose.

8. A method for the alleviation of depression in a living animal body subject thereto which comprises the step of administering to the living animal body an amount of a compound of claim 2 which is effective for said purpose.

9. Method of claim [10] *7* wherein the compound is administered in the form of a pharmaceutical composition thereof.

10. Method of claim 8 wherein the compound is administered in the form of a pharmaceutical composition thereof.

11. A method for the preparation of a compound as defined in claim 1, which comprises, converting substantially, pure [(+)-4-(4-dimethylamino)-1-(4'-fluorophenyl)-1-(hydroxybutyl)-3-(hydroxymethyl)-benzonitrile] *(−)-4-[4-(dimethylamino)-1-(4'-fluorophenyl)-1-*hydroxy-*1-butyl]-3-(hydroxymethyl)-benzonitrile* or a [monomester] *monoester* thereof in a stereoselective way to substantially pure (+)-1-(3-dimethylaminopropyl)-1-(4'-fluorophenyl)-1,3-dihydroisobenzofuran-5-carbonitrile which is isolated as such or as a non-toxic acid addition salt thereof.

12. A compound of the formula *(31)-Enantiomer of the compound 4-[4-(dimethylamino)-1-(4'-fluorophenyl)-1-hydroxy-1-butyl]-3-(hydroxymethyl)-benzonitrile or an ester of said (−)enantiomer, which has the formula*

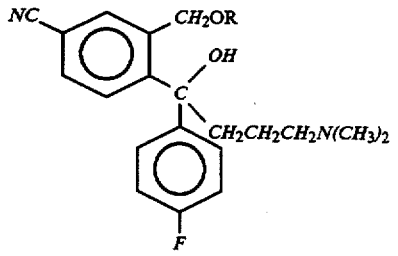

wherein R is hydrogen or represents a group completing a labile ester.

* * * * *

UNITED STATES PATENT AND TRADEMARK OFFICE

CERTIFICATE OF CORRECTION

PATENT NO. : Re.34,712

DATED : August 30, 1994

INVENTOR(S) : Klaus Boegesoe, Jens K. Perregaard

It is certified that error appears in the above-indentified patent and that said Letters Patent is hereby corrected as shown below:

Column 1, line 40; "aqeuous" should read -- aqueous --
Column 1, line 43; "]salt]" should read -- [salt] --
Column 2, line 2; "Scan.," should read -- Scand., --
Column 4, line 1; move the words "REACTION SCHEME II" down to line 55 to be together with the formulae which follow.
Column 6, line 4; "99.0%" should read -- 99.9% --
Column 7, line 62; "(10 nm)" should read -- (10 nM) --
Column 11, line 16; Before "12." insert a bold -- [ -- and after the word "formula" insert a bold -- ] --
Column 11, line 16; After "formula" and Before "(31)" insert the following.

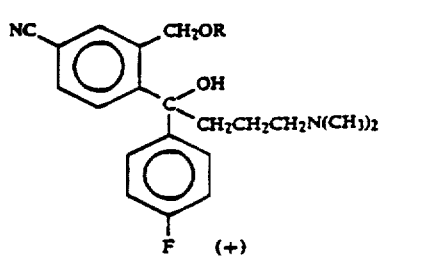

II wherein R is hydrogen or represents a group completing a labile ester.

* * * * *

UNITED STATES PATENT AND TRADEMARK OFFICE

CERTIFICATE OF CORRECTION

PATENT NO. : Re. 34,712

DATED : August 30, 1994

INVENTOR(S) : Klaus Boegesoe, Jens K. Perregaard

It is certified that error appears in the above-indentified patent and that said Letters Patent is hereby corrected as shown below:

Column 11, lines 16 and 17; delete the rest of this line 16, namely: "(31)-Enantiomer of" and delete line 17 and rewrite in *italics* *as lines 40 and 41 as follows:*

*-- 12. (-) - Enantiomer of the compound 4-[4-(dimethylamino)-1-(4'-fluorophenyl)- --*

Column 12, lines 15 & 16 should be in *italics*.

Signed and Sealed this

Second Day of January, 1996

*Attest:*

Bruce Lehman

BRUCE LEHMAN

*Attesting Officer*

*Commissioner of Patents and Trademarks*